US005116978A

United States Patent [19]

Mathiaparanam

[11] Patent Number: 5,116,978

[45] Date of Patent: May 26, 1992

[54] PROCESS FOR BIS(INDOLYL)ETHYLENE SYNTHESIS

[75] Inventor: Ponnampalam Mathiaparanam, Appleton, Wis.

[73] Assignee: Appleton Papers Inc., Appleton, Wis.

[21] Appl. No.: 615,731

[22] Filed: Nov. 19, 1990

Related U.S. Application Data

[63] Continuation-in-part of Ser. No. 320,642, Mar. 8, 1989, Pat. No. 4,996,328.

[51] Int. Cl.[5] .......... C07D 413/00

[52] U.S. Cl. .......... 544/144; 544/142; 544/143; 546/200; 546/201; 548/452; 548/454; 548/455

[58] Field of Search .......... 548/455, 454, 452; 544/142, 143, 144; 546/200, 201

[56] References Cited

U.S. PATENT DOCUMENTS

| | | | |
|---|---|---|---|
| 4,016,174 | 8/1978 | Farber | 548/456 |
| 4,020,056 | 4/1977 | Farber | 548/456 |
| 4,020,068 | 4/1977 | Farber | 548/345 |
| 4,022,771 | 5/1977 | Farber | 548/456 |
| 4,107,428 | 8/1978 | Farber | 542/437 |
| 4,119,776 | 10/1978 | Farber | 544/405 |
| 4,349,679 | 9/1982 | Garner et al. | 546/196 |
| 4,795,736 | 1/1989 | Hung et al. | 428/913 |
| 4,812,569 | 3/1989 | Eckstein | 548/456 |
| 4,897,494 | 1/1990 | Psaar | 548/455 |
| 4,931,567 | 6/1990 | Psaar | 548/455 |

FOREIGN PATENT DOCUMENTS

| | | |
|---|---|---|
| 0242169 | 4/1987 | European Pat. Off. . |
| 0325708 | 11/1987 | European Pat. Off. . |

OTHER PUBLICATIONS

Chemical Abstracts, vol. 112:22353(a), "Bis(3-Indolyl-)ethylene Dye Intermediates".

Saxton, J. E., J. Chem. Soc. 3592 (1952).

Kiang, A. K. & Mann, F. G., J. Chem. Soc. 594 (1953).

Angeli, A. & Marchetti, G., Atti. Accad. Lineci, 16 & Chem. Abstr., 2.

Borsche, W. & Groth, H. Anralen Chem. Abstr., vol. 37, 3754 (1943).

Mueller, J. et al., Chem. Abstracts, vol. 103, No. 1, ref. 6178F.

Pindur, U. et al., Chem. Abstracts, vol. 108, No. 17, ref. 150225O.

*Primary Examiner*—Marianne Cintins

*Assistant Examiner*—Jessica H. Nguyen

*Attorney, Agent, or Firm*—Benjamin Mieliulis

[57] ABSTRACT

A process for producing a bis-(indolyl)ethylene of the formula

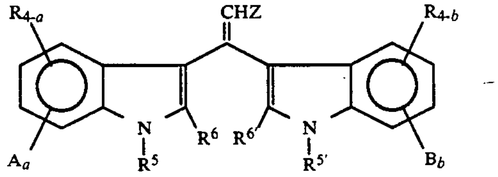

is described, wherein A, B, a, b, R, Z, $R^{5'}$, $R^6$ and $R^{6'}$ are as defined in the specification, said method comprising reacting an indole of the formula

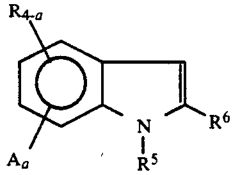

with an acylindole of the formula

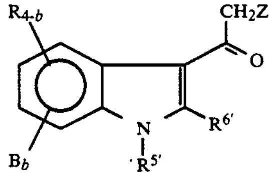

in the presence of a Vilsmeier reagent selected from the group consisting of phosphoryl chloride, phosgene, oxalyl chloride, benzoyl chloride, thionyl chloride, alkanesulfonyl chloride, arene-sulfonyl chloride, alkylchoroformate, and arylchloroformate, together with a Lewis Acid selected from the group consisting of zinc chloride, boron trifluoride and aluminum chloride.

6 Claims, 2 Drawing Sheets

Fig. 1a
Scheme A
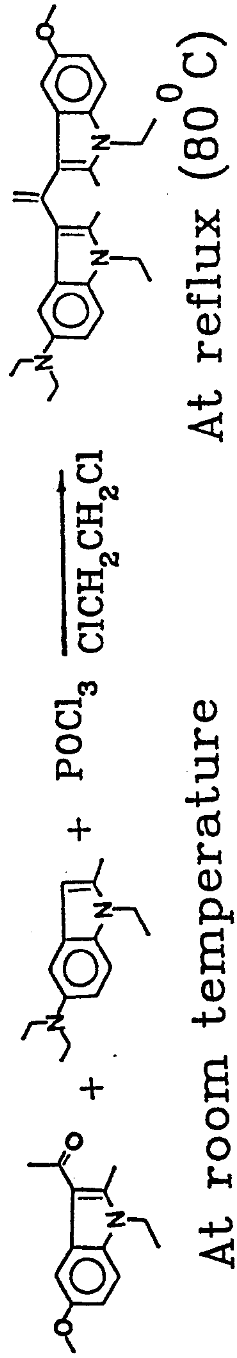
At room temperature
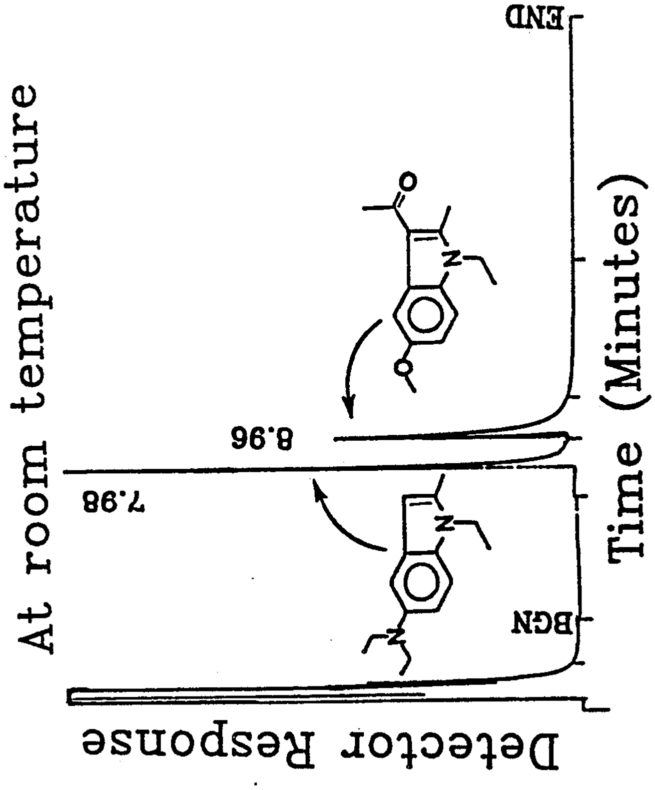
Fig. 1b
At reflux ($80^0C$)
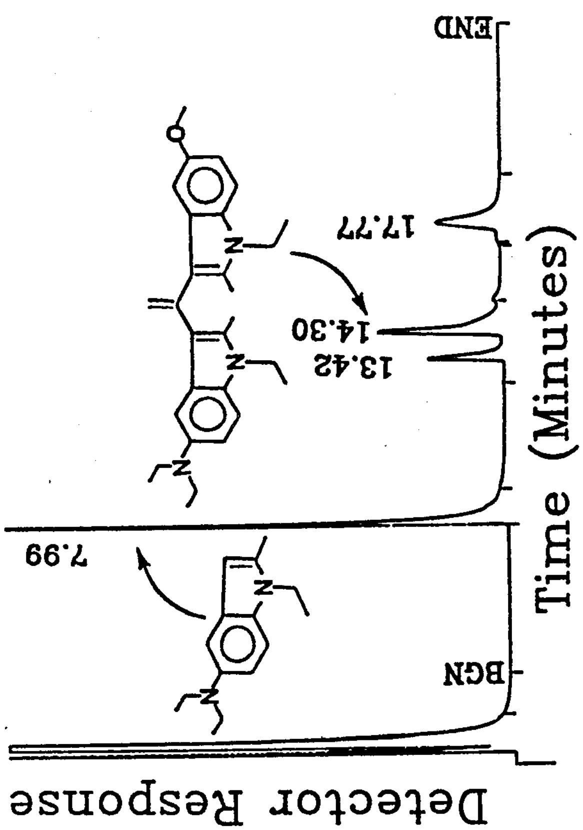
Fig. 1c Fig. 2a
Scheme B
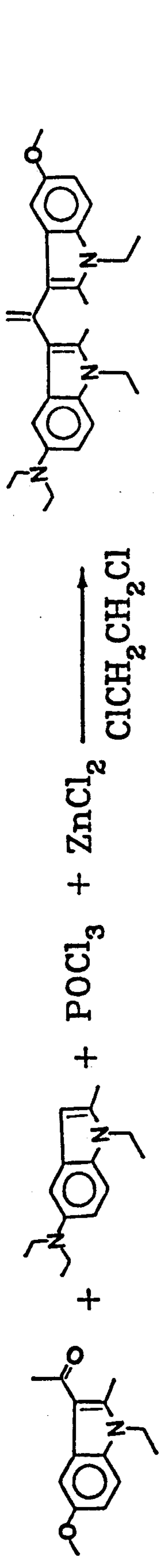
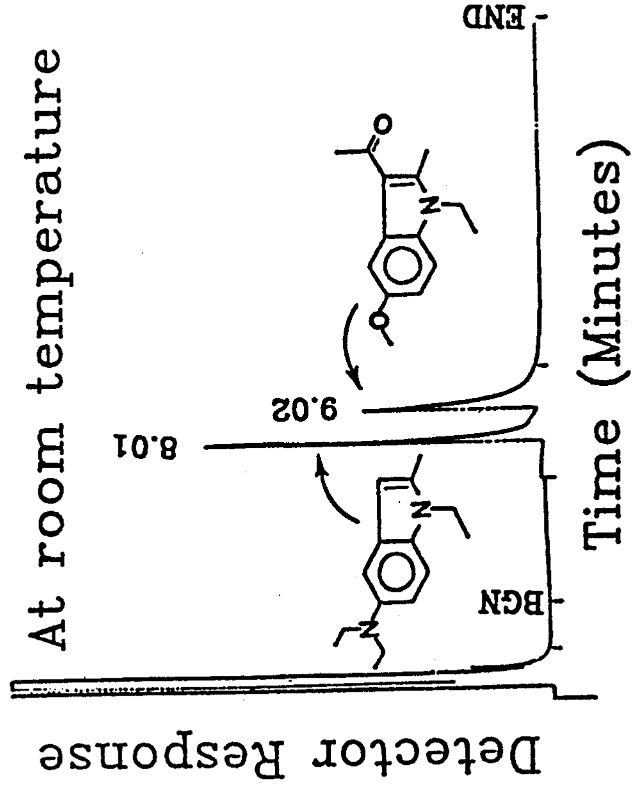
Fig. 2b
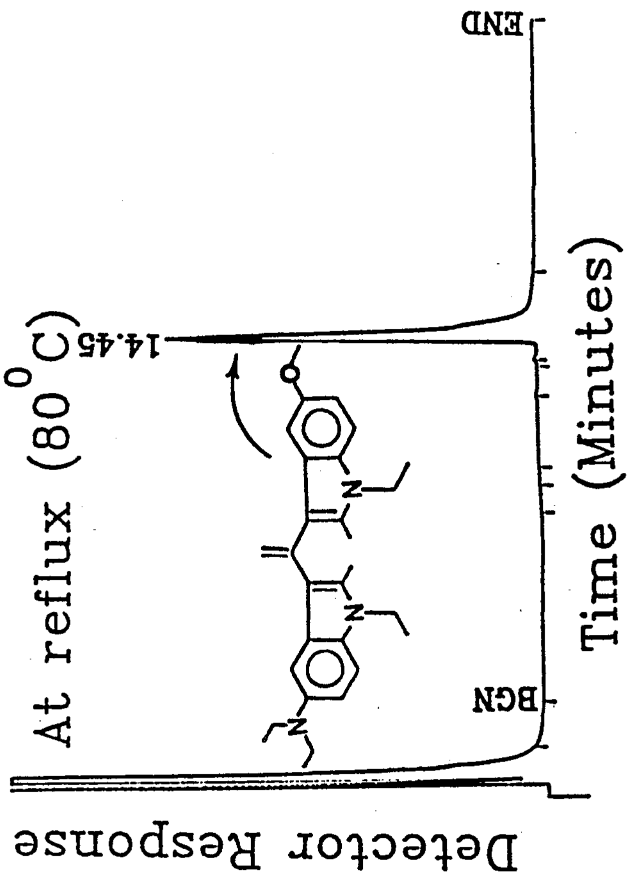
Fig. 2c

PROCESS FOR BIS(INDOLYL)ETHYLENE SYNTHESIS

This application is a continuation-in-part of Ser. No. 320,642 filed Mar. 8, 1989, now U.S. Pat. No. 4,996,328.

FIELD OF INVENTION

1. Background of Invention

This invention relates to bis-(indolyl)ethylenes, particularly methods for their production. The color-formers or chromogenic compounds are substantially colorless or light-colored but form more pronounced colors when reacted with an electron accepting material.

2. Description of Related Art

Several divinyl phthalide chromogenic compounds (C1) [(C) $L^1$,$L^2$=substituted phenyl] (read as compound C1 arrived at by referring to formula C wherein $L^1$ and $L^2$ are as stated) have been prepared by the condensation of ethylenes (A1) [(A) $L^1$,$L^2$=substituted phenyl] with phthalic anhydrides (B1) [(B) Each Halogen is independently Cl or Br] in acetic anhydride (Sheldon Farber, U.S. Pat. Nos. 4,020,056, 4,022,771, 4,107,428, 4,119,776;)

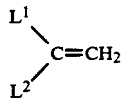
(A)

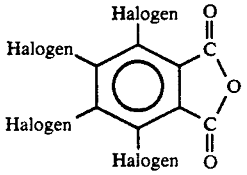
(B)

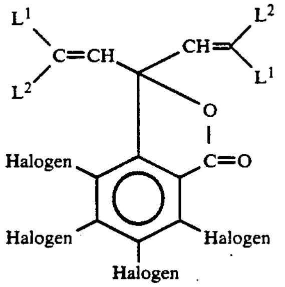
(C)

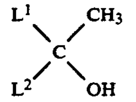
(D)

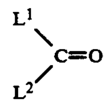
(E)

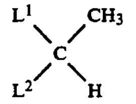
(F)

Substituted ethylenes (A1) or their precursors (D1) [(D) $L^1$,$L^2$=substituted phenyl] were prepared by the reaction of methylmagnesium bromide (also known as methyl Grignard reagent) with ketones (E1) [(E) $L^1$,$L^2$=substituted phenyl]. The use of a Grignard reaction to prepare A1) imposes severe restrictions on the scaleup synthesis of (A1) and consequently on the manufacture of divinyl phthalides (C1).

In another synthetic approach, the alcohol (D1) was obtained by reacting the ethane (F1) [(F) $L^1$,$L^2$ =substituted phenyl] with lead peroxide in either nitric acid or formic acid; and the substituted ethylene (A) was obtained from (D1) by dehydration [Yamada Kagaku, Japan Kokai 1988-8360, filed Jun. 30, 1986].

When indole was heated with acetic anhydride containing 10% acetic acid a bis-(indolyl)ethylene (A2) [(A) $L^1$,$L^2$=1-acetylindole-3-yl] apparently was obtained as a by-product in 5–10% yield (J. E. Saxton, J. Chem. Soc., 3592 (1952)].

Substituted (2- and 1,2-) indoles when reacted with acetyl cyanide in the presence of hydrogen chloride yielded 1-cyano-1,1-di(indole 3-yl)ethanes (G) and apparently some of these products may be converted to bis-(indolyl)ethylenes (H) by heating them under vacuum either alone or with soda lime. In some cases, dependent on certain select substituents M and W, (G) may yield some (H) type compounds on refluxing with aqueous-ethanolic 10% potassium hydroxide [A. K. Kiang and F. G. Mann, J. Chem., Soc., 594 (1953)].

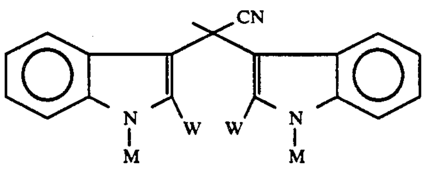
(G)

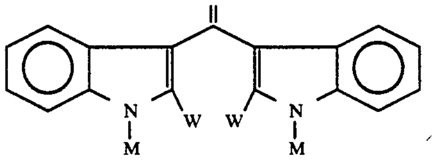
(H)

M = H, Ph
W = Me, Ph

Bis-(indolyl)ethylene (H1) [(H) M=H and W=Me] was speculated to be a product (m.p. 203° C.) from the reaction of 2-methylindole with ethyl acetate and sodium ethoxide. No other data were given to substantiate the structure [A. Angeli and G. Marchetti, Atti. Accad. Lincei, 16 (II), 179 (1907)].

In another report (W. Borsche and H. Groth, Annalen, 549, 238 (1941)], 2-methylindole when boiled with acetyl chloride formed a product that on treatment with alkali gave a pseudobase, ($C_{20}H_{18}N_2$, pale rose, m.p. 208° C.). The pseudobase was suggested to be 1-(2-methylindole-3-yl)-1-(2-methyl-3-indolidene)ethane (H2). Again, insufficient data precludes the substantiation of this structure. Furthermore, similar structure was proposed for the pseudobase obtained by substituting 2-phenylindole for 2-methylindole.

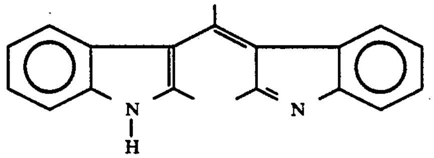
(H2)

U.S Pat. Nos. 4,897,494 and 4,931,567 disclose several symmetrical bis-(indolyl)ethylene compounds. Unsymmetrical types of bis-(indolyl)ethylenes are not taught or suggested.

BRIEF DESCRIPTION OF THE DRAWINGS

FIG. 1, comprised of FIGS. 1*a*, 1*b*, and 1*c*, is a gas chromatograph instrument printout of the reaction mixture of an indole with an acylindole in the presence of the Vilsmeier reagent, phosphoryl chloride.

FIG. 2, comprised of FIGS. 2*a*, 2*b*, and 2*c*, is a gas chromatograph printout of the product of reaction mixture of an indole with an acylindole in the presence of the Vilsmeier reagent, phosphoryl chloride and the Lewis Acid, zinc chloride. Note magnitude of bis indolylethylene—attributed peak in FIG. 2*c* as compared to FIG. 1*c*.

DETAILED DESCRIPTION OF THE INVENTION

This invention teaches an improved process for producing bis(indolyl)ethylenes. The process comprises reacting an indole of the formula

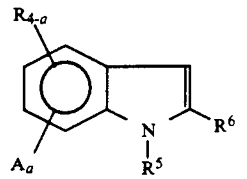

with an acylindole of the formula

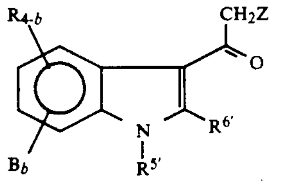

in the presence of a Vilsmeier reagent such as phosphoryl chloride, phosgene, oxalyl chloride, benzoyl chloride, thionylchloride, alkanesulfonyl chloride, arenesulfonyl chloride, alkyl chloroformate or aryl chloroformate together with a Lewis acid such as zinc chloride or aluminum chloride. The reaction can be run with or without solvent. Preferred Vilsmeier reagents are phosphoryl chloride, ethyl chloroformate, thionyl chloride, and diethyl chlorophosphate. More preferred is phosphenyl chloride.

In the process of the invention bis-(indolyl)ethylenes of the following formula are prepared:

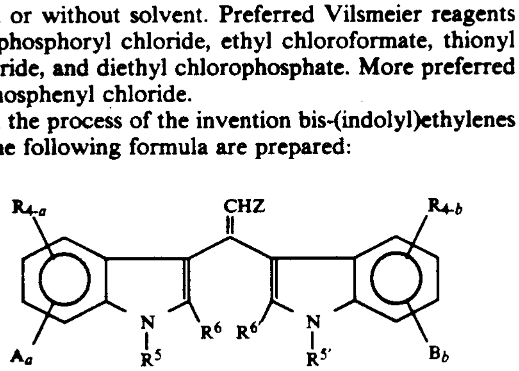

wherein a is 1 or 2,
wherein b is 1 or 2,
wherein each A is independently selected from a dialkylamino, dialkoxyalkylamino, diaroxyalkylamino, diarylamino, alkylarylamino, dicycloalkylamino, alkylcycloalkylamino, arylcycloalkylamino, pyrrolidino, piperidino, or morpholino radical,
wherein each B is independently selected from A or an alkoxy, alkoxyalkyl or aroxy radical,
wherein each R is independently selected from hydrogen, halogen, alkyl or alkoxy,
wherein each of $R^5$, $R^{5'}$, $R^6$ and $R^{6'}$ are each independently selected from hydrogen, alkyl($C_1$-$C_8$), alkoxyalkyl, aroxyalkyl, cycloalkyl ($C_3$-$C_6$), phenyl, and phenyl substituted by alkyl($C_1$-$C_8$) or alkoxy ($C_1$-$C_8$),
wherein Z is selected from hydrogen, alkyl($C_1$-$C_8$), alkoxyalkyl, aroxyalkyl, halogen, phenyl or phenyl substituted by alkyl or alkoxy,
the alkyl moieties referred to herein being of one to eight carbons, the cycloalkyl moieties referred to herein being of three to six carbons.

With the pyrrolidino, piperidino or morpholino groups, the following are preferred:

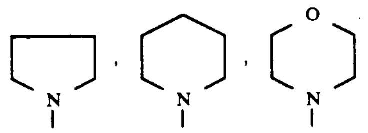

Bonding through sites other than the nitrogen atom can be accomplished for these groups but yields appear reduced.

Vilsmeier reagents include:

| | | |
|---|---|---|
| (a) | Diethyl Chlorophosphate | $(EtO)_2POCl$ |
| (b) | Phosphoryl Chloride | $POCl_3$ |
| (c) | Ethyl Chloroformate | $EtOCOCl$ |
| (d) | Oxalyl Chloride | $(COCl)_2$ |
| (e) | Thionyl Chloride | $SOCl_2$ |
| (f) | Phosgene Iminium Chloride | $[Cl_2C{=}N(CH_3)_2]^+Cl^-$ |
| (g) | Phenyl Dichlorophosphate | $PhOPOCl_2$ |

(a) to (c) of the Vilsmeier reagents are preferred. (d) to (g) find use with aroxy bearing reactants, but are typically too active for alkoxy bearing reactants.

Lewis Acids are substances that coordinate with an electron pair to form a complex. Lewis Acids include $ZnCl_2$, $BF_3$ preferably as the etherate, $AlCl_3$ and the like. $ZnCl_2$ is preferred herein.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes can be made by those skilled in the art without departing from the spirit and scope of the invention. Unless otherwise indicated, all measurements are on the basis of weight and in the metric system.

EXAMPLE 1

Condensation of 5-diethylamino-1-ethyl-2-methylindole with 3-acetyl-1-ethyl-5-methoxy-2-methylindole using Phosphoryl chloride

[Scheme A, FIG. 1]

5-Diethylamino-1-ethyl-2-methylindole(1.2 g, 5 mmoles), 3-acetyl-1-ethyl-5-methoxy-2-methylindole(1.4 g, 6 mmoles) and Phosphoryl chloride(0.8 g, 5.2 mmoles) in 1,2-dichloroethane(20 ml) was stirred at room temperature in a flask equipped with a magnetic stirrer and a reflux condenser carrying a drying tube. After two hours, the gas chromatographic analysis of the reaction mixture indicated no reaction, only the starting materials were present. Then, the reaction mixture the reaction mixture was refluxed overnight and monitored by gas chromatography. The reaction mixture contained a mixture of products: 5-diethylamino-1-ethyl-2-methylindole(one of the starting materials), 1-(5-diethylamino-1-ethyl-2-methylindole-3-yl)-1-(1-ethyl-5-methoxy-2-methylindole-3-yl)ethylene (expected product) and two other unidentified products.

EXAMPLE 2

Condensation of 5-diethylamino-1-ethyl-2-methylindole with 3-acetyl-1-ethyl-5-methoxy-2-methylindole using Phosphoryl chloride and zinc chloride

[Scheme B, FIG. 2]

5-Diethylamino-1-ethyl-2-methylindole(230 mg, 1 mmole),3-acetyl-1-ethyl-5-methoxy-2-methylindole(250 mg, 1.08 mmoles), Phosphoryl chloride(170 mg, 1.1 mmoles) and zinc chloride(150 mg, 1.1 mmoles) in 1,2-dichloroethane(5 ml) was stirred at room temperature in a flask equipped with a magnetic stirrer and a reflux condenser carrying a drying tube. After two hours, gas chromatographic analysis of the reaction mixture indicated no reaction. Then, the reaction mixture was refluxed overnight and monitored by gas chromatography. The reaction mixture contained 1-(5-diethylamino-1-ethyl-2-methylindole-3-yl)-1-(1-ethyl-5-methoxy-2-methylindole-3-yl)ethylene as the major product.

What is claimed is:

1. A process for producing a bis-(indolyl)ethylene of the formula

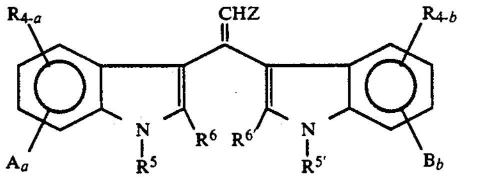

wherein a is 1 or 2, wherein b is 1 or 2, wherein each A is selected from the group consisting of a dialkylamino, dialkoxyalkylamino, diaroxyalkylamino, diarylamino, alkylarylamino, dicycloalkylamino, alkylcycloalkylamino, arylcycloalkylamino, pyrrolidino, piperidino, and morpholino radical, wherein each B is selected from the group consisting of A, alkoxy, alkoxyalkyl and aroxy radical, wherein each R is selected from the group consisting of hydrogen, halogen, alkyl, and alkoxy, wherein each of $R^5$, $R^{5'}$, $R^6$, and $R^{6'}$ are selected from the group consisting of hydrogen, alkyl ($C_1$-$C_8$), alkoxyalkyl, aroxyalkyl, cycloalkyl ($C_3$-$C_6$), phenyl, and phenyl substituted by alkyl ($C_1$-$C_8$) or alkoxy ($C_1$-$C_8$), wherein Z is selected from the group consisting of hydrogen, alkyl ($C_1$-$C_8$), alkoxyalkyl, aroxyalkyl, halogen, phenyl, and phenyl substituted by alkyl or alkoxy, the alkyl moieties referred to herein being of one to eight carbons, the cycloalkyl moieties referred to herein being of three to six carbons, said method comprises reacting an indole of the formula

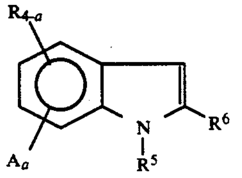

with an acylindole of the formula

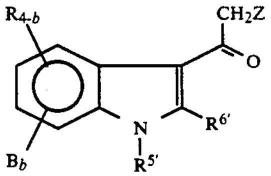

in the presence of a Vilsmeier reagent selected from the group consisting of phosphoryl chloride, phosgene, oxalyl chloride, benzoyl chloride, thionyl chloride, alkanesulfonyl chloride, arenesulfonyl chloride, alkylchloroformate, and arylchloroformate, together with a Lewis Acid selected from the group consisting of zinc chloride, boron trifluoride, and aluminum chloride.

2. The process according to claim 1 wherein the Vilsmeier reagent is phosphoryl chloride.

3. The process according to claim 1 wherein the Vilsmeier reagent is diethyl chlorophosphate.

4. The process according to claim 1 wherein the Vilsmeier reagent is ethyl chloroformate.

5. The process according to claim 1 wherein the reaction of indole with acylindole is carried out in an organic solvent.

6. The process according to claim 5 wherein the solvent is dichloroethane.

* * * * *